United States Patent [19]

Tsubaki et al.

[11] Patent Number: 4,960,794

[45] Date of Patent: Oct. 2, 1990

[54] TRIGLYCERIDES HAVING STABILITY WITH LAPSE OF TIME AND METHOD FOR STABILIZATION THEREOF

[75] Inventors: Nobuyuki Tsubaki; Yoshio Nakano, both of Nishinomiya, Japan

[73] Assignee: Nippon Oil and Fats Co., Ltd., Tokyo, Japan

[21] Appl. No.: 252,633

[22] Filed: Oct. 3, 1988

[30] Foreign Application Priority Data

Oct. 8, 1987 [JP] Japan .................................. 62-252369

[51] Int. Cl.$^5$ ..................... A61K 31/225; C07C 67/29; C07C 3/02
[52] U.S. Cl. ..................................... 514/547; 560/263; 260/410.7; 260/410.8
[58] Field of Search ................ 514/786, 547; 560/263; 260/410.7, 410.8

Primary Examiner—Douglas W. Robinson
Assistant Examiner—Raymond J. Henley III
Attorney, Agent, or Firm—Jordan and Hamburg

[57] ABSTRACT

Triglycerides are stabilized by preventing hydrolysis of triglycerides. A method for stabilizing triglycerides comprises controlling a polymorphic composition of the triglycerides so that the polymorphic composition includes either 10 to 30% by weight of $\alpha$ type, 20 to 40% by weight of $\beta'$ type and 40 to 60% by weight of $\beta$ type or 35 to 55% by weight of $\beta'$ type and 45 to 65% by weight of $\beta$ type.

34 Claims, 2 Drawing Sheets

DSC CURVE AFTER COOLING IN COMPARATIVE EXAMPLE 1

DSC CURVE AFTER AGEING IN EXAMPLE 1

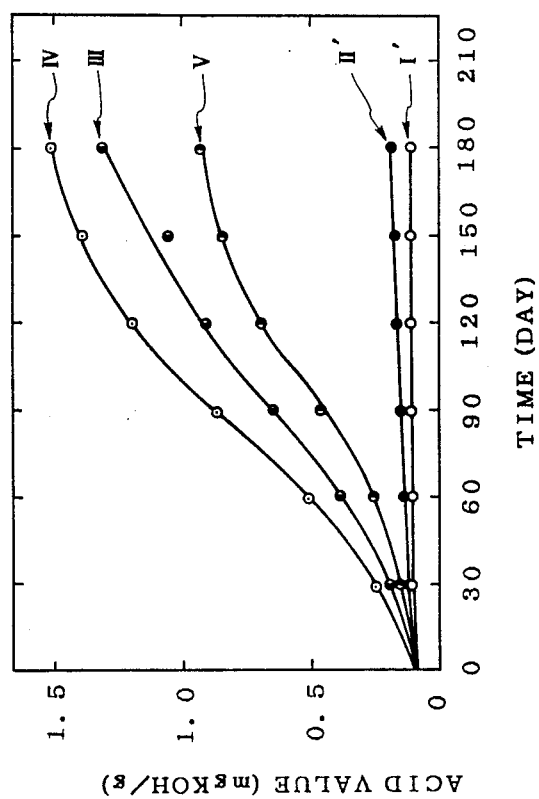

TRIGLYCERIDES HAVING STABILITY WITH LAPSE OF TIME AND METHOD FOR STABILIZATION THEREOF

BACKGROUND OF THE INVENTION:

This invention relates to triglycerides having stability with lapse of time, and a method for stabilization thereof. More particularly, it relates to triglycerides having stability with lapse of time, such as properties of preventing hydrolysis and stabilizing the melting point, and the method for stabilization thereof.

Triglycerides, that is oils and fats, have so far been produced from naturally found materials, and are used in a variety of applications, such as in industrial usage or for foods, cosmetics and medicines. In recent years, synthetic triglycerides obtained by esterification of fatty acids and glycerin, or so-called synthetic lipids, have attracted attention with respect to their physical and chemical properties, and are employed as a base for cosmetics and medicines.

However, triglycerides are known to undergo hydrolysis with lapse of time, as evidenced by the hydrolysis of edible oils and fats (see "J. Japan Oil Chem. Soc.", vol.26, page 150 (1977)), deterioration of shortening, butter and margarine (vol. 16, page 13, (1967), ibid) and deterioration of hardened coconut oil (vol.16, page 506, (1967), ibid). Such hydrolysis of triglycerides with lapse of time occurs not only in natural oils and fats, but also in synthetic oils and fats, with the result that free fatty acids are formed to give rise to deficiencies such as disagreeable smells and degradation in quality. For these reasons, methods have been proposed in recent years for preventing hydrolysis of triglycerides for realizing stability of the triglycerides with lapse of time, such as, for example, methods of random-interesterification ("J. Japan Oil Chem. Soc.", vol.18, page 730 (1969)), addition of liquid oils (vol.19, page 397, (1970), ibid) or addition of surfactants (vol.21, page 888, (1972), ibid).

However, although the hydrolysis of triglycerides with lapse of time is ascribable to polymorphism specific to the triglycerides, the situation is that account has not been taken sufficiently of the polymorphism in the aforementioned conventional methods for preventing the hydrolysis. Therefore, these conventional methods for preventing the hydrolysis have a drawback that, while they have some effects on natural oils and fats, they do not have sufficient effects on synthetic oils and fats. With the addition of the liquid oils or surfactants, it is necessary to add considerable amounts of these agents, since the addition of small amounts gives only limited effects. Hence, the properties natural to the triglycerides are impaired such that the triglycerides cannot be used as a base for cosmetics or medicines. Hence, the situation is that, while there is a strong demand for triglycerides free from hydrolysis with lapse of time and having superior stability with lapse of time, the triglycerides fully meeting these requirements have not yet been produced.

SUMMARY OF THE INVENTION:

It is a principal object of the present invention to provide a method for stabilizing triglycerides by preventing hydrolysis of triglycerides.

It is another object of the present invention to provide triglycerides having stability with lapse of time, such as properties of preventing hydrolysis, whether the triglycerides are of natural or synthetic origin.

It is a further object of the present invention to provide triglycerides having stability with lapse of time and utilizable as base materials for cosmetics or medicines, above all, as suppositories, and a method for stabilization thereof.

It is still another object of the present invention to provide triglycerides having stability with lapse of time and a stable melting point and that can be stored for prolonged time without regard to temperature.

The above and other objects of the invention will become apparent from the following description.

According to the present invention, there is provided a method for stabilizing triglycerides by preventing hydrolysis of the triglycerides, comprising controlling a polymorphic composition of the triglycerides so that the polymorphic composition includes 10 to 30% by weight of $\alpha$ type, 20 to 40% by weight of $\beta'$ type and 40 to 60% by weight of $\beta$ type, the $\alpha$ type, the $\beta'$ type and the $\beta$ type making up 100% by weight.

According to the present invention, there are also provided triglycerides having stability with lapse of time comprising 10 to 30% by weight of an $\alpha$ type triglyceride polymorph, 20 to 40% by weight of a $\alpha$ type triglyceride polymorph and 40 to 60% by weight of a $\beta'$ type polymorph, the $\alpha$ type, $\beta'$ type and $\beta$ type triglyceride polymorphs making up 100% by weight.

According to the present invention, there is also provided a method for stabilizing triglycerides by preventing hydrolysis of the triglycerides, comprising controlling a polymorphic composition of the triglycerides so that the polymorphic composition includes 35 to 55% by weight of $\beta'$ type and 45 to 65% by weight of $\beta$ type, the $\beta'$ type and the $\beta$ type making up 100% by weight.

According to the present invention, there are further provided triglycerides having stability with lapse of time comprising 35 to 55% by weight of a $\beta'$ type triglyceride polymorph and 45 to 65% by weight of a $\beta$ type triglyceride polymorph, the $\beta'$ type and $\beta$ type triglyceride polymorphs making up 100% by weight.

BRIEF DESCRIPTION OF THE DRAWINGS:

FIG. 3 is a graph showing the relation between the acid value and the elapsing time in days of triglycerides in Tables 4 and 6, with the curves I' and II' and III to V in FIG. 3 corresponding to the curves I to V in FIGS. 1 and 2, respectively.

Figure 2:
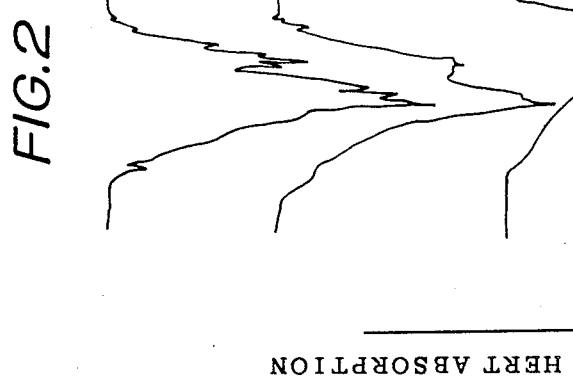
FIG. 2 is a chart showing DSC curves for triglycerides cooled in comparative Example 1 in a manner not in meeting with the present invention.

PREFERRED EMBODIMENTS OF THE INVENTION:

The present inventors have found that, for realizing stability with lapse of time of triglycerides, it suffices to control the polymorphism peculiar to triglycerides by a specific operation. The present invention has been fulfilled on the basis of this finding. A more detailed description of the crystalline structure and the polymorphism peculiar to the triglycerides is given hereinbelow.

In general, there are presently known three different types of polymorphs in the triglycerides, namely $\alpha$ type, $\beta'$ type and $\beta$ type, the melting points of which become higher in this sequence. As the triglycerides are rapidly cooled and solidified from the state of melted liquid, the α type having subcells of the hexagonal system is precipitated. Crystal transition then occurs towards the β' type intermediate polymorph of the rhombic system type with increase in temperature and then towards the β type polymorph of the triclinic system, which represents the most stable polymorph, with further increase in temperature. This transition is irreversible, such that, once the transition has been made to the β type, the most stable polymorph, reversion to the former polymorph does not occur even when the temperature is lowered, since the crystal free energy of the polymorphs is decreased in the order of the α type, the β' type and the β type. It will be observed that the crystal transition from the α type to the β' type and thence to the β type or from the α type to the β type depends on the conditions of the processing temperatures and the triglyceride composition and proceeds in accordance with one of the three different basic processes of (a) α-solid-state transition, (b) fusion-recrystallization transition and (c) oil-mediated transition ("YUSHI", vol.38, page 67, (1985)). By (a) the α-solid-state transition is meant the transition of the triglycerides due to molecular rearrangement of the triglycerides in the crystalline state at the temperatures not higher than the melting points of the polymorphs. By (b) the fusion-recrystallization transition is meant a phenomenon in which, whilst the different polymorphs are maintained at the temperatures intermediate between the respective melting points, a polymorph having the lower melting point is melted and a polymorph having the higher melting point is generated as nuclei and grown. Finally, by (c) the oil-mediated transition is meant a phenomenon in which, whilst two kinds of the polymorphs in the crystalline phase at the temperature not higher than the melting points are dispersed in the liquid oil, transition of the solute occurs from the melted unstable polymorphs towards the stable polymorphs through the oil phase.

The hydrolysis with the lapse of time and unstable melting point of the triglyceride products, that detract from stability of triglycerides with lapse of time, may be ascribable to the above described crystal transition. More specifically, the αtype and the β' type, the unstable polymorphs, undergo crystal transition with lapse of time towards the β type, the stable polymorph, with release of the heat of transition at the time of such transition. By this heat of transition, the triglycerides are hydrolyzed as they react with water existing among the crystals. The β type, the most stable polymorph, does not undergo crystal transition. It is, however, extremely difficult and takes a lot of time to produce the impeccable β type from the melted liquid, such that the precipitated β type crystals tend to become excessively coarse in size to deteriorate the physical properties of the ultimate products. Therefore, in order to prevent hydrolysis with lapse of time of triglycerides and to provide stability with lapse of time with triglycerides, it is necessary that the crystal transition be suppressed completely.

For suppressing the crystal transition, it is effective to direct attention to the bonds of the triglyceride molecules and to allow the formation of mixed polymorphs to provide strong and intimate bonds at the terminal molecules of the polymorphs in the course of crystallization ("YUSHI", vol.38, page 66, (1985)). There are presently known methods for forming the mixed polymorphs, such as the methods of i) adding diglycerides to triglycerides (J. Sci., Food, Agric., 32, 1197 (1981)), ii) admixing triglycerides of unsaturated fatty acids to triglycerides of saturated fatty acids and iii) providing difference in the number of carbon atoms of the fatty acids of triglycerides.

With these methods, crystal transition can be suppressed to some extent by modifying the state of bonding at the terminal groups of the triglyceride molecules. However, it is only possible with these known methods to lower the rate of hydrolysis, while it is not possible to prevent crystal transition completely. These methods are not desirable since it is unnecessary to use any additives when the mixed polymorphs are to be used as the bases for cosmetics or medicaments. For these reasons, there are presently demanded mixed polymorphs that do not necessitate the use of additives when the polymorphs are used as the bases for cosmetics or medicaments and that are completely free from crystal transition.

For studies and investigations in polymorphism in general, DSC, X-ray diffractiometry, polarimetric infrared spectrometry or Raman spectrometry, are being employed, whereby it has become possible to obtain information concerning the construction of the polymorphs, or to make an analysis of the crystalline structure, see "YUSHI", vol.38, page 81 (1985).

The triglycerides having stability with lapse of time according to the present invention are free from hydrolysis with lapse of time, can be stored for prolonged time and have a stable melting point. It can be prepared while the relative ratio of the α type, β' type and β type polymorphs is controlled to provide strong and stable bonds of the respective polymorphs. More specifically, in a case where the polymorphic composition contains mixed polymorphs of α type, β' type and β type, it is desirable, for example, to maintain a melted liquid of triglycerides at a temperature not higher than the melting point of the α type, preferably at a temperature of 1 to 5° C. lower than the melting point of the α type, for 6 to 24 hours, thereby to control the crystallization of the α type. It is also desirable to carry out sampling at this time and to make an analysis as to whether the amount of the α type present in the melted liquid is in the range of from 10 to 35% by weight, with the aid of DSC, X-ray diffraction, polarimetric infrared spectrum or Raman spectrum. It is then desirable to maintain the resulting solid at an intermediate temperature between the melting point of the α type and the melting point of the β' type for preferably 6 to 24 hours to control the crystallization of the β' type. It is preferred that the aforementioned sampling operation be carried out at this time to make an analysis by the aforementioned analytic methods as to whether the amount of the α type and the amount of the β' type are within the ranges of from 10 to 35 by weight and 20 to 45% by weight, respectively. It is desirable that the solid is then maintained at an intermediate temperature between the melting point of the β' type and the melting point of the β type preferably for 6 to 24 hours to control the crystallization of the β type. It is also desirable that the aforementioned sampling operation be again carried out in order to make an analysis with the aid of the aforementioned methods as to whether the amounts of the α type, β' type and β type are in the ranges of from 10 to 30% by weight, 20 to 40% by weight and 40 to 60% by weight, respectively, with the amounts of the αtype, the β' type and the β type making up 100% by weight. Briefly, the triglycerides having stability with the lapse of time can be formed by setting the amounts of the respective polymorphs to the above defined ranges by the above described stabilization methods. With the amounts of the α type, β' type and β type polymorphs outside the above defined ranges, stability with lapse of time, such as the stable melting point or the stable bonding sufficient to prevent hydrolysis of triglycerides, cannot be obtained.

In a case where a polymorphic composition contains mixed polymorphs of the β' type and the β type, it is preferred that a melted liquid of triglycerides be maintained at the temperature not higher than the melting point of the β' type and desirably 1 to 5° C. lower than the melting point of the β' type for 6 to 24 hours to thereby control crystallization of the β' type. It is preferred that the aforementioned sampling operation be carried out at this time to make an analysis by DSC, X-ray diffraction, polarimetric infrared spectrum or Raman spectrum as to whether the amount of the β' type is within the range of from 35 to 60% by weight. It is desirable that the resulting solid is then maintained at an intermediate temperature between the melting point of the β' type and the melting point of the β type for preferably 6 to 24 hours to control the crystallization of the β type. It is also desirable that the aforementioned sampling operation is again carried out in order to make an analysis with the aid of the aforementioned methods as to whether the amounts of the β' type and the β type are in the ranges of from 35 to 55% by weight and 45 to 65% by weight, respectively, with the amounts of the β' type and the β type making up 100% by weight. By setting the amount of the polymorphic composition by the above described stabilization method in the manner as described above, triglycerides having stability with lapse of time can be produced. With the amounts of the polymorphic β' type and β type outside the above defined ranges, it is undesirably not possible to provide stability with lapse of time such as the stable bond sufficient to prevent hydrolysis of triglycerides or stable melting point.

It will be noted that, although only one operation of controlling the amount ratio of the α type, the β' type and the β type or the amount ratio of the β' type and the β type suffices, it may also be desirable to carry out the processes several times, above all, two or three times, for increasing the amount of the β type to thereby stabilize triglycerides as well as reducing the reaction time duration necessary to produce the β type polymorph.

In setting the intermediate temperatures between the melting points for the α-β'-β type polymorphs and for the β'-β type polymorphs, the intermediate temperature between the melting point of the α type and that of the β' type, for example, is desirably so set as to be not lower than the melting point of the α type and 1 to 5 ° C. lower than the melting point of the β' type, while the intermediate temperature between the melting point of the β' type and that of the β type is desirably so set as to be not lower than the melting point of the β' type and 1 to 5° C. lower than the melting point of the β type.

The triglycerides of the present invention are preferably selected from the group consisting of triglycerides of single fatty acids, triglycerides of mixed fatty acids, a glyceride mixture containing not more than 10 by weight of diglycerides and a glyceride mixture containing not more than 10% by weight of monoglycerides, and preferably have the iodine value of not more than 5 and the hydroxyl value of not more than 15. The triglycerides of single fatty acids are preferably selected from the group consisting of caproic acid, caprylic acid, capric acid, lauric acid, myristic acid, palmitic acid, stearic acid and arachic acid.

The triglycerides employed in accordance with the present invention may be synthesized as conventionally. For polishing and preventing cracking of triglycerides, surfactants selected from the group consisting of not more than 0.5% by weight of sucrose fatty acid esters, sorbitan fatty acid esters, polyoxyethylene alkylethers, polyoxyethylene polyalcohol fatty acid esters and mixtures thereof may be contained.

The triglycerides having stability with lapse of time and the method for stabilization thereof according to the present invention are highly useful industrially in that the hydrolysis with lapse of time of triglycerides can be prevented in an extremely simple manner and the melting point of the triglyceride products can be stabilized for extended time, by a simple operation of crystallizing the triglycerides by a predetermined sequence of operations.

The triglycerides having stability with lapse of time and the method for stabilization thereof according to the present invention are effective not only for natural oils and fats but also for synthetic oils and fats and may be applied advantageously as the bases for cosmetics or medicines since, above all, the additives are not necessitated.

The triglycerides of the present invention having stability with lapse of time are substantially free from crystal transition, so that the problem of increasing the melting point, hitherto thought to be inherent in triglycerides, can be eliminated simultaneously. For this reason, it may be advantageously employed in suppositories for which the melting point represents a crucial factor.

The triglycerides of the present invention having stability with lapse of time may be stored for prolonged time at room temperature without refrigeration since the crystal transition can be prevented in an extremely simple manner without regard to the temperatures.

EXAMPLES OF THE INVENTION:

The present invention will be explained with reference to the Examples and Comparative Examples.

EXAMPLE 1

The compositions of the fatty acids, acid values (AV), hydroxyl values (OHV) and the melting points of the α type, the β' type and the β type of the triglycerides employed in the Example, are as shown in Table 1.

The triglycerides shown in Table 1 were melted and crystallized in accordance with the present invention. The conditions are shown in Table 2. Each operation of crystallization was carried out in the direction of the arrow marks in Table 2 for the ageing time intervals shown in Table 2. The numbers of times of ageing are also indicated in Table 2. For example, the No.1 sample in Table 2 was aged at 25° C. for 12 hours, then aged at 30° C. for 12 hours and aged at 33° C. for 12 hours. The above operational sequence was repeated twice.

Figure 1:
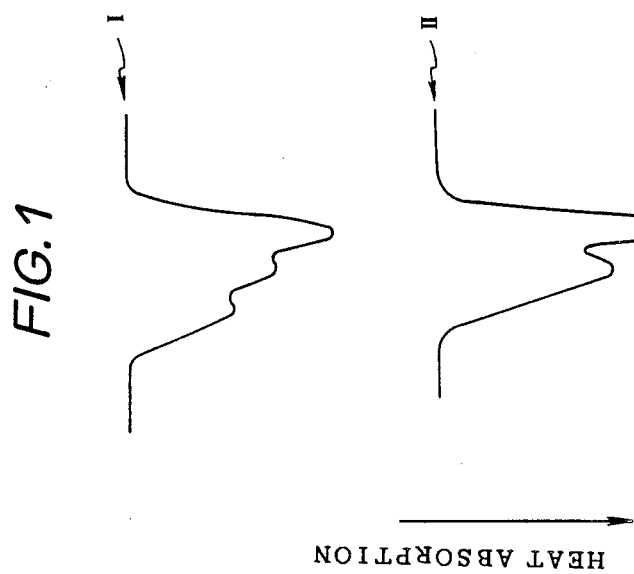
FIG. 1 is a chart showing DSC curves for triglycerides crystallized in accordance with Example 1 of the present invention.

The triglycerides shown in Table 2 were maintained at a constant temperature in a hermetically sealed vessel and measurements were made of the polymorphic compositions and the acid values. The results are shown in Tables 3 and 4 and in FIG. 3. Each of the polymorphic compositions was found by accurately weighing about 5 mg of each of the samples, cutting out a DSC chart when the temperature was raised from 10° C. at the rate of 0.5° C. per minute and measuring the weight ratios of the produced crystals at the peaks of heat absorption. The results are shown in FIG. 1.

It is seen from Table 3 that the triglycerides crystallized in accordance with the present invention are substantially free from crystal transition, while it is seen from Table 4 that the triglycerides are actually superior in stability with lapse of time and, above all, free from hydrolysis with lapse of time.

COMPARATIVE EXAMPLE 1

The triglyceride samples shown in Table 1 were melted and cooled to various temperatures, and the polymorphic compositions thereof were found by the method shown in Example 1. The results are shown in Table 5 and in FIG. 2.

Then the triglyceride samples shown in Table 4 were maintained at constant temperatures shown in Table 6 in a hermetically sealed container and the acid values thereof were measured periodically. The results are shown in Table 6 and in FIG. 3.

It is seen from Table 6 that, unless the ageing operation of the present invention is carried out, the acid values are actually increased, while the hydrolysis occurs with lapse of time.

TABLE 2

Crystallization Conditions in Example 1

| No. | Sample | Temp. (°C.) | Ageing Duration (Hr) | Number of Times |
|---|---|---|---|---|
| 1 | TG-1 | 25→30→33 | 12 | 2 |
| 2 | TG-1 | 30→33 | 12 | 2 |
| 3 | TG-2 | 15→21→28 | 12 | 2 |
| 4 | TG-2 | 21→28 | 12 | 2 |
| 5 | TG-2 | 34→38→43 | 12 | 2 |
| 6 | TG-3 | 38→43 | 12 | 2 |

TABLE 3

Changes in Polymorphic Composition in Example 1

| | | Polymorphic Composition | | | | | |
|---|---|---|---|---|---|---|---|
| | | Early Stage | | | 6 Months | | |
| No. | Samples | α Type (%) | β' Type (%) | β Type (%) | α Type (%) | β' Type (%) | β Type (%) |
| 1-1 | TG-1 | 21.2 | 31.0 | 47.8 | 20.8 | 30.5 | 48.7 |
| 1-2 | TG-1 | 21.2 | 31.0 | 47.8 | 20.6 | 31.1 | 48.3 |
| 2-1 | TG-1 | — | 44.8 | 55.2 | — | 43.5 | 56.5 |
| 2-2 | TG-1 | — | 44.8 | 55.2 | — | 44.4 | 55.6 |
| 3-1 | TG-2 | 15.1 | 26.7 | 58.2 | 14.8 | 27.0 | 58.2 |
| 3-2 | TG-2 | 15.1 | 26.7 | 58.2 | 14.4 | 26.8 | 58.8 |
| 4-1 | TG-2 | — | 39.4 | 60.6 | — | 38.1 | 61.9 |
| 4-2 | TG-2 | — | 39.4 | 60.6 | — | 38.2 | 61.8 |
| 5-1 | TG-3 | 27.5 | 28.6 | 43.9 | 27.2 | 27.4 | 45.4 |
| 5-2 | TG-3 | 27.5 | 28.6 | 43.9 | 26.7 | 28.4 | 44.9 |
| 6-1 | TG-3 | — | 50.3 | 49.7 | — | 49.5 | 50.5 |
| 6-2 | TG-3 | — | 50.3 | 49.7 | — | 48.6 | 51.4 |

TABLE 4

Tests on Stability with Lapse of Time of Acid Value in Example 1

| | | Maintaining Temp. | Acid Value (mgKOH/g) | | |
|---|---|---|---|---|---|
| No. | Samples | (°C.) | Early Stage | 3 Months | 6 Months |
| 1-1 | TG-1 | 5 | 0.10 | 0.10 | 0.10 |
| 1-2 | TG-1 | 25 | 0.10 | 0.13 | 0.16 |
| 2-1 | TG-1 | 5 | 0.10 | 0.11 | 0.13 |
| 2-2 | TG-1 | 25 | 0.10 | 0.15 | 0.18 |
| 3-1 | TG-2 | 5 | 0.10 | 0.12 | 0.12 |
| 3-2 | TG-2 | 25 | 0.10 | 0.14 | 0.17 |
| 4-1 | TG-2 | 5 | 0.10 | 0.12 | 0.14 |
| 4-2 | TG-2 | 25 | 0.10 | 0.12 | 0.16 |
| 5-1 | TG-3 | 5 | 0.10 | 0.11 | 0.13 |
| 5-2 | TG-3 | 25 | 0.10 | 0.14 | 0.19 |
| 6-1 | TG-3 | 5 | 0.10 | 0.12 | 0.13 |
| 6-2 | TG-3 | 25 | 0.10 | 0.14 | 0.16 |

TABLE 1

Triglycerides Subjected to Tests

| | Fatty Acid Composition (%) | | | | | | | Acid Value | Hydroxyl Value | Melting Point (°C.) | | |
|---|---|---|---|---|---|---|---|---|---|---|---|---|
| Sample | *c8 | c10 | c12 | c14 | c16 | c18 | c20 | (AV) | (OHV) | α Type | β' Type | β Type |
| TG-1 | — | — | 56.3 | 20.4 | 11.6 | 11.7 | — | 0.10 | 4.7 | 28.7 | 31.9 | 35.2 |
| TG-2 | 8.1 | 8.0 | 50.3 | 13.9 | 9.9 | 9.7 | — | 0.10 | 7.8 | 18.8 | 26.1 | 31.3 |
| TG-3 | — | — | 33.3 | 14.7 | 20.5 | 27.5 | 3.9 | 0.10 | 13.4 | 36.2 | 41.5 | 45.4 |

*c8; Caprylic acid, c10; Capric acid, c12; Lauric acid, c14; Myristic acid, c16; Palmitic acid, c18; Stearic acid, c20; Arachic acid

TABLE 5

Crystallization Conditions and Polymorphic Composition in Comparative Example 1

| | | Cooling | | Polymorphic Compsition | | |
|---|---|---|---|---|---|---|
| No. | Sample | Temp. (°C.) | Duration (Hr) | α Type (%) | β' Type (%) | β Type (%) |
| 7 | TG-1 | −20 | 12 | 76.3 | 23.7 | — |
| 8 | TG-1 | 10 | 24 | 70.6 | 28.1 | 1.3 |
| 9 | TG-1 | 30 | 48 | 7.8 | 15.9 | 76.3 |
| 10 | TG-2 | 0 | 24 | 64.1 | 35.9 | — |
| 11 | TG-2 | 20 | 48 | 3.1 | 10.8 | 86.1 |
| 12 | TG-3 | 10 | 24 | 54.3 | 29.5 | 16.2 |

TABLE 5-continued

Crystallization Conditions and Polymorphic Composition in Comparative Example 1

| No. | Sample | Cooling Temp. (°C.) | Duration (Hr) | α Type (%) | β' Type (%) | β Type (%) |
|---|---|---|---|---|---|---|
| 13 | TG-3 | 35 | 48 | 8.4 | 16.3 | 75.3 |

TABLE 6

Tests on Stability with Lapse of Time of Acid Value in Comparative Example 1

| No. | Samples | Maintaining Temp. (°C.) | Acid Value (mgKOH/g) Early Stage | 3 Months | 6 Months |
|---|---|---|---|---|---|
| 7-1 | TG-1 | 5 | 0.10 | 0.65 | 1.32 |
| 7-2 | TG-1 | 25 | 0.10 | 0.98 | 1.79 |
| 8-1 | TG-1 | 5 | 0.10 | 0.86 | 1.52 |
| 8-2 | TG-1 | 25 | 0.10 | 0.91 | 1.82 |
| 9-1 | TG-1 | 5 | 0.10 | 0.46 | 0.93 |
| 9-2 | TG-1 | 25 | 0.10 | 0.69 | 1.35 |
| 10-1 | TG-2 | 5 | 0.10 | 0.57 | 1.12 |
| 10-2 | TG-2 | 25 | 0.10 | 0.42 | 0.95 |
| 11-1 | TG-2 | 5 | 0.10 | 0.75 | 1.26 |
| 11-2 | TG-2 | 25 | 0.10 | 0.55 | 1.05 |
| 12-1 | TG-3 | 5 | 0.10 | 0.71 | 1.47 |
| 12-2 | TG-3 | 25 | 0.10 | 0.58 | 1.15 |
| 13-1 | TG-3 | 5 | 0.10 | 0.63 | 1.47 |
| 13-2 | TG-3 | 25 | 0.10 | 0.83 | 1.64 |

EXAMPLE 2

The triglyceride samples shown in Table 1 were heated and melted at 50° C. and admixed with medicaments, namely indomethacin and phenobarbital. Each of the resulting mixtures was stirred thoroughly and cast into a suppository mold so that 25 mg of the medicaments are contained in 1 g of triglycerides. The samples TG-1, TG-2 and TG-3 were crystallized under the conditions of the present invention as shown in Table 2, No.1, Table 2, No. 3 and Table 2, No.5, respectively, and stored at the prescribed temperatures shown in Table 7. The melting points were then measured periodically. The results are shown in Table 7, along with those of the samples not containing the medicaments.

It is noted that the melting points were measured in accordance with A.O.C.S. Official Method Cc 1-25, while the samples were taken out or sampled by directly introducing a capillary into the suppositories.

It is seen from Table 7 that the melting points of the suppositories of the present invention are not increased but remain constant so that the suppositories of the present invention are excellent in stability with lapse of time.

COMPARATIVE EXAMPLE 2

The suppository samples were prepared and the melting points thereof were measured periodically in the same way as in Example 2 except that the samples were cooled and solidified at 0° C. for 12 hours and thus without following the conditions of the present invention shown in Table 2. The results are shown in Table 8.

It is seen from Table 8 that the melting points are actually raised when the operation is not made in accordance with the present invention.

TABLE 7

Test on Stability with Lapse of Time of Melting Point in Example 2

| Sample | Medicament | Maintaining Temp. (°C.) | Melting Point (°C.) Early Stage | 3 Months | 6 Months |
|---|---|---|---|---|---|
| TG-1 | — | 5 | 36.4 | 36.4 | 36.4 |
| TG-1 | — | 25 | 36.4 | 36.4 | 36.4 |
| TG-1 | IM | 5 | 36.4 | 36.4 | 36.4 |
| TG-1 | IM | 25 | 36.4 | 36.4 | 36.5 |
| TG-1 | FB | 5 | 36.5 | 36.5 | 36.5 |
| TG-1 | FB | 25 | 36.5 | 36.5 | 36.6 |
| TG-2 | — | 5 | 32.3 | 32.3 | 32.3 |
| TG-2 | IM | 5 | 32.4 | 32.4 | 32.5 |
| TG-2 | FB | 5 | 32.3 | 32.3 | 32.4 |
| TG-3 | — | 25 | 47.1 | 47.1 | 47.2 |
| TG-3 | IM | 25 | 47.1 | 47.2 | 47.2 |
| TG-3 | FB | 25 | 47.2 | 47.2 | 47.3 |

IM: Indomethacin
FB: Phenobarbital

TABLE 8

Tests on Stability with Lapse of Melting Point in Comparative Example 2

| Sample | Medicament | Maintaining Temp. (°C.) | Melting Point (°C.) Early Stage | 3 Months | 6 Months |
|---|---|---|---|---|---|
| TG-1 | — | 5 | 35.4 | 36.8 | 37.0 |
| TG-1 | — | 25 | 35.4 | 36.9 | 37.0 |
| TG-1 | IM | 5 | 35.5 | 36.9 | 36.9 |
| TG-1 | IM | 25 | 35.5 | 37.0 | 37.1 |
| TG-1 | FB | 5 | 35.4 | 36.8 | 36.9 |
| TG-1 | FB | 25 | 33.4 | 36.9 | 37.0 |
| TG-2 | — | 5 | 31.1 | 32.6 | 32.9 |
| TG-2 | IM | 5 | 31.1 | 32.7 | 32.8 |
| TG-2 | FB | 5 | 31.2 | 32.7 | 32.9 |
| TG-3 | — | 25 | 45.8 | 47.5 | 47.6 |
| TG-3 | IM | 25 | 45.7 | 47.4 | 47.5 |
| TG-3 | FB | 25 | 45.7 | 47.5 | 47.5 |

IM: Indomethacin
FB: Phenobarbital

Although the present invention has been described with reference to the specific examples, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A composition comprising triglycerides having stability with lapse of time comprising 10 to 30% by weight of an α type triglyceride polymorph, 20 to 40% by weight of a β' type triglyceride polymorph and 40 to 60% by weight of a β type triglyceride polymorph, the α type, β' type and β type triglyceride polymorphs making up 100% by weight, each % by weight being based on the total weight of the αtype, β' type and β type triglyceride polymorphs.

2. The composition according to claim 1, wherein said triglycerides are selected from the group consisting of triglycerides of single fatty acids, triglycerides of mixed fatty acids, a glyceride mixture comprising not more than 10% by weight of diglycerides and a glyceride mixture comprising not more than 10% by weight of monoglycerides, said triglycerides having the iodine value of not more than 5 and the hydroxyl value of not more than 15.

3. The composition according to claim 2 wherein the triglycerides of said single fatty acids are selected from the group consisting of triglycerides of caproic acid, caprylic acid, capric acid, lauric acid, myristic acid, palmitic acid, stearic acid and arachic acid.

4. The composition according to claim 1 further comprising surfactants in an amount of not more than 0.5% by weight based on the total weight of the composition.

5. The composition according to claim 4 wherein said surfactants are selected from the group consisting of sucrose fatty acid esters, sorbitan fatty acid esters, polyoxyethylene akylethers, polyoxyethylene polyalcohol fatty acid esters and mixtures thereof.

6. A composition comprising triglycerides having stability with lapse of time comprising 35 to 55% by weight of a $\beta''$ type triglyceride polymorph and 45 to 65% by weight of a $\beta$ type triglyceride polymorph, the $\beta'$ type, and the $\beta$ type triglyceride polymorphs making up 100% by weight, each % by weight being based on the total weight of the $\beta'$ type and $\beta$ type triglyceride polymorphs.

7. The composition according to claim 6, wherein said triglycerides are selected from the group consisting of triglycerides of single fatty acids, triglycerides of mixed fatty acids, a glyceride mixture comprising not more than 10% by weight of diglycerides and a glyceride mixture comprising not more than 10% by weight of monoglycerides, said triglycerides having the iodine value of not more than 5 and the hydroxyl value of not more than 15.

8. The composition according to claim 7 wherein the triglycerides of said single fatty acids are selected from the group consisting of triglycerides of caproic acid, caprylic acid, capric acid, lauric acid, myristic acid, palmitic acid, stearic acid and arachic acid.

9. The composition according to claim 6 further wherein said triglycerides further contain surfactants in an amount of not more than 0.5% by weight based on the total weight of the composition.

10. The composition according to claim 9 wherein said surfactants are selected from the group consisting of sucrose fatty acid esters, sorbitan fatty acid esters, polyoxyethylene akylethers, polyoxyethylene polyalcohol fatty acid esters and mixtures thereof.

11. A method for stabilizing triglycerides subject to hydrolytic destabilization by preventing hydrolysis of said triglycerides, comprising the steps of:
(a) maintaining a melted liquid comprising said triglycerides at a temperature 1 to 5° C. lower than the melting point of an $\alpha$ type triglyceride polymorph for 6 to 24 hours;
(b) then maintaining said triglycerides at a temperature not lower than the melting point of the $\alpha$ type triglyceride polymorph and 1 to 5° C. lower than the melting point of a $\beta'$ type triglyceride polymorph for 6 to 24 hours; and
(c) finally maintaining said triglycerides at a temperature not lower than the melting point of the $\beta'$ type triglyceride polymorph and 1 to 5° C. lower than the melting point of a $\beta$ type triglyceride polymorph for 6 to 24 hours, whereby a polymorphic composition of said triglycerides comprises 10 to 30% by weight of the $\alpha$ type triglyceride polymorph, 20 to 40% by weight of the $\beta'$ type triglyceride polymorph and 40 to 60% by weight of the $\beta$ type triglyceride polymorph, the $\alpha$ type triglyceride polymorph, the $\beta'$ type triglyceride polymorph and the $\beta$ type triglyceride polymorph making up 100% by weight, each % by weight being based on the total weight of the $\alpha$ type, $\beta'$ type and $\beta$ type triglyceride polymorphs.

12. The method according to claim 11 further comprising a step (d) of maintaining said triglycerides from said step (c) at said temperature 1 to 5° C. lower than the melting point of the $\alpha$ type triglyceride polymorph for 6 to 24 hours and then effecting said steps (b) and (c) with optional repeating of said steps (d), (b) and (c).

13. The method according to claim 11 further comprising the steps of sampling said triglycerides after each of the steps (a) to (c) and analyzing amounts of the respective triglyceride polymorphs.

14. The method according to claim 12 further comprising the steps of sampling said triglycerides after each of the steps (a) to (d) and analyzing amounts of the respective triglyceride polymorphs.

15. The method according to claim 13 wherein said analyzing step is performed based on analysis selected from the group consisting of the DSC method, X-ray diffractiometry, polarimetric infrared spectrometry and Raman spectrometry.

16. The method according to claim 14 wherein said analyzing step is performed based on analysis selected from the group consisting of the DSC method, X-ray diffractiometry, polarimetric infrared spectrometry and Raman spectrometry.

17. The method according to claim 13 wherein the amount of the $\alpha$ type triglyceride polymorph is 10 to 35% by weight after said step (a), the amounts of the $\alpha$ type triglyceride polymorph and the $\beta'$ type triglyceride polymorph are 10 to 35% by weight and 20 to 45% by weight, respectively, after said step (b) and the amounts of the $\alpha$ type triglyceride polymorph, the $\beta'$ type triglyceride polymorph and the $\beta$ type triglyceride polymorph are 10 to 30% by weight, 20 to 40% by weight and 40 to 60% by weight, respectively, after said step (c), with the $\alpha$ type triglyceride polymorph, the $\beta'$ type triglyceride polymorph and the $\beta$ type triglyceride polymorph making up 100% by weight, each % by weight being based on the total weight of the triglycerides.

18. The method according to claim 14 wherein the amount of the $\alpha$ type triglyceride polymorph is 10 to 35% by weight after said step (d), the amounts of the $\alpha$ type triglyceride polymorph and the $\beta'$ type triglyceride polymorph are 10 to 35% by weight and 20 to 45% by weight, respectively, after said step (b) and the amounts of the $\alpha$ type triglyceride polymorph, the $\beta'$ type triglyceride polymorph and the $\beta$ type triglyceride polymorph are 10 to 30% by weight, 20 to 40% by weight and 40 to 60% by weight, respectively, after said step (c), with the $\alpha$ type triglyceride polymorph, the $\beta'$ type triglyceride polymorph and the $\beta$ type triglyceride polymorph making up 100% by weight, each % by weight being based on the total weight of the triglycerides.

19. The method according to claim 11 wherein said triglycerides are selected from the group consisting of triglycerides of single fatty acids, triglycerides of mixed fatty acids, a glyceride mixture comprising not more than 10% by weight of diglycerides and a glyceride mixture comprising not more than 10% by weight of monoglycerides, said triglycerides having the iodine value of not more than 5 and the hydroxyl value of not more than 15.

20. The method according to claim 19 wherein the triglycerides of said single fatty acids are selected from the group consisting of triglycerides of caproic acid, caprylic acid, capric acid, lauric acid, myristic acid, palmitic acid, stearic acid and arachic acid.

21. The method according to claim 11 wherein said triglycerides are in admixture with surfactants in an amount of not more than 0.5% by weight based on the total weight of the admixture.

22. The method according to claim 21 wherein said surfactants are selected from the group consisting of sucrose fatty acid esters, sorbitan fatty acid esters, polyoxyethylene akylethers, polyoxyethylene polyalcohol fatty acid esters and mixtures thereof.

23. A method for stabilizing triglycerides subject to hydrolytic destabilization by preventing hydrolysis of said triglycerides, comprising the steps of:
(a) maintaining a melted liquid comprising said triglycerides at a temperature 1 to 5 20 C. lower than the melting point of an $\beta'$ type triglyceride polymorph for 6 to 24 hours; and
(b) then maintaining said triglycerides at a temperature not lower than the melting point of the $\beta'$ type triglyceride polymorph and 1 to 5° C. lower than the melting point of a $\beta$ type triglyceride polymorph for 6 to 24 hours,
whereby a polymorphic composition of said triglycerides comprises 35 to 55% by weight of the $\beta$ type triglyceride polymorph and 45 to 65% by weight of the $\beta$ type triglyceride polymorph, the $\beta'$ type triglyceride polymorph and the $\beta$ type triglyceride polymorph making up 100% by weight, each % by weight being based on the total weight of the $\beta'$ type and $\beta$ type and $\beta$ type triglyceride polymorphs.

24. The method according to claim 23 further comprising a step (c) of maintaining said triglycerides from said step (b) at said temperature 1 to 5° C. lower than the melting point of the $\beta'$ type triglyceride polymorph for 6 to 24 hours and then effecting said steps (b) with optional repeating of said steps (c) and (b).

25. The method according to claim 23 further comprising the steps of sampling said triglycerides after each of the steps (a) to (b) and analyzing amounts of the respective triglyceride polymorphs.

26. The method according to claim 24 further comprising the steps of sampling said triglycerides after each of the steps (a) to (c) and analyzing amounts of the respective triglyceride polymorphs.

27. The method according to claim 25 wherein said analyzing step is performed based on analysis selected from the group consisting of the DSC method, X-ray diffractiometry, polarimetric infrared spectrometry and Raman spectrometry.

28. The method according to claim 26 wherein said analyzing step is performed based on analysis selected from the group consisting of the DSC method, X-ray diffractiometry, polarimetric infrared spectrometry and Raman spectrometry.

29. The method according to claim 25 wherein the amount of the $\beta'$ type triglyceride polymorph is 35 to 60% by weight after said step (a), the amounts of the $\beta'$ type triglyceride polymorph and the $\beta$ type triglyceride polymorph are 35 to 55% by weight and 45 to 65% by weight, respectively, after said step (b) and the amounts of the $\beta'$ type triglyceride polymorph and the $\beta$ type triglyceride polymorph and the $\beta$ type triglyceride polymorph making up 100% by weight, each % by weight being based on the total weight of the triglycerides.

30. The method according to claim 26 wherein the amount of the $\beta$ type triglyceride polymorph is 35 to 60% by weight after said step (c), the amounts of the $\beta'$ type triglyceride polymorph and the $\beta$ type triglyceride polymorph are 35 to 55% by weight and 45 to 65% by weight, respectively, after said step (b), with the $\beta'$ type triglyceride polymorph and the $\beta$ type triglyceride polymorph making up 100% by weight, each % by weight being based on the total weight of the triglycerides.

31. The method according to claim 23 wherein said triglycerides are selected from the group consisting of triglycerides of single fatty acids, triglycerides of mixed fatty acids, a glyceride mixture comprising not more than 10% by weight of diglycerides and a glyceride mixture comprising not more than 10% by weight of monoglycerides, said triglycerides having the iodine value of not more than 5 and the hydroxyl value of not more than 15.

32. The method according to claim 31 wherein the triglycerides of said single fatty acids are selected from the group consisting of triglycerides of caproic acid, caprylic acid, capric acid, lauric acid, myristic acid, palmitic acid, stearic acid and arachic acid.

33. The method according to claim 23 wherein said triglycerides are in admixture with surfactants in an amount of not more than 0.5% by weight based on the total weight of the admixture.

34. The method according to claim 33 wherein said surfactants are selected from the group consisting of sucrose fatty acid esters, sorbitan fatty acid esters, polyoxyethylene akylethers, polyoxyethylene polyalcohol fatty acid esters and mixtures thereof.

* * * * *